United States Patent
Klitzke et al.

(10) Patent No.: US 11,026,980 B1
(45) Date of Patent: Jun. 8, 2021

(54) FLOWABLE BIRTH TISSUE COMPOSITION AND RELATED METHODS

(71) Applicant: Triad Life Sciences, Inc., Memphis, TN (US)

(72) Inventors: Kurt Klitzke, Memphis, TN (US); Jon G. Hargis, Memphis, TN (US)

(73) Assignee: Triad Life Sciences, Inc., Memphis, TN (US)

( * ) Notice: Subject to any disclaimer, the term of this patent is extended or adjusted under 35 U.S.C. 154(b) by 0 days.

(21) Appl. No.: 16/284,443

(22) Filed: Feb. 25, 2019

Related U.S. Application Data

(60) Provisional application No. 62/635,091, filed on Feb. 26, 2018.

(51) Int. Cl.
| | | |
|---|---|---|
| *A61K 35/50* | (2015.01) | |
| *C12N 5/073* | (2010.01) | |
| *A61L 27/36* | (2006.01) | |
| *A61P 17/02* | (2006.01) | |

(52) U.S. Cl.
CPC .......... *A61K 35/50* (2013.01); *A61L 27/3604* (2013.01); *A61L 27/3687* (2013.01); *C12N 5/0605* (2013.01); *A61L 2400/06* (2013.01); *A61P 17/02* (2018.01); *C12N 2539/00* (2013.01)

(58) Field of Classification Search
CPC ................ A61K 35/60; A61K 27/3604; A61K 2400/06; C12N 5/0605
See application file for complete search history.

(56) References Cited

U.S. PATENT DOCUMENTS

| | | |
|---|---|---|
| 4,647,283 A | 3/1987 | Carpentier et al. |
| 6,203,755 B1 | 3/2001 | Odland |
| 7,795,493 B2 | 9/2010 | Phelps et al. |
| 8,106,251 B2 | 1/2012 | Ayares et al. |
| 9,642,937 B2 | 5/2017 | Zhao et al. |
| 9,808,491 B2 | 11/2017 | Tseng et al. |
| 2015/0086634 A1* | 3/2015 | Koob ..................... A61Q 19/08 424/489 |
| 2015/0182664 A1 | 7/2015 | Ayares et al. |
| 2015/0216957 A1* | 8/2015 | Markosian ......... A61K 39/0005 424/85.2 |
| 2016/0129049 A1* | 5/2016 | Tseng ..................... A61K 35/48 424/445 |

FOREIGN PATENT DOCUMENTS

| | | |
|---|---|---|
| EP | 0738106 B1 | 8/2001 |
| WO | 2003030949 A1 | 4/2003 |
| WO | 2012141454 A2 | 10/2012 |
| WO | 2015017500 A1 | 2/2015 |
| WO | 2017017474 A1 | 2/2017 |
| WO | 2017076782 A1 | 5/2017 |

OTHER PUBLICATIONS

Arachea, B.T., et al., "Detergent selection for enhanced extraction of membrane proteins", Protein Expression and Purification, (2012), vol. 86, pp. 12-20.

* cited by examiner

*Primary Examiner* — Marcia S Noble
(74) *Attorney, Agent, or Firm* — Barnes & Thornburg LLP

(57) ABSTRACT

A flowable birth tissue composition fabricated from birth tissue is provided. Methods of processing a mammal's placental tissue to form a flowable birth tissue composition are provided. Various methods of treatment and uses are also provided.

10 Claims, No Drawings

US 11,026,980 B1

FLOWABLE BIRTH TISSUE COMPOSITION AND RELATED METHODS

CROSS-REFERENCE TO RELATED APPLICATIONS

The present application claims priority to U.S. Provisional Application No. 62/635,091 filed Feb. 26, 2018, the content of which is incorporated herein in its entirety.

BACKGROUND OF THE INVENTION

Human placental tissue has been utilized for various purposes over the past century for regenerative medicine purposes. There remains a need, however, for regenerative products derived from alternative sources and alternative methods.

SUMMARY OF THE INVENTION

The present invention is generally directed to a flowable birth tissue composition, processes for producing the flowable birth tissue composition, and methods of use. The flowable birth tissue composition exhibits various regenerative medical properties. The flowable birth tissue may be placed in, placed on or injected within areas of a patient in need.

According to one aspect, a flowable birth tissue composition is provided that includes porcine placental tissue. According to one embodiment, the porcine placental tissue includes at least one placental membrane, at least one amnion membrane, at least one chorion membrane, at least one intermediate layer, at least one placental globe, at least one umbilical cord, at least one amniotic fluid, or any combination thereof. According to one embodiment, the flowable birth tissue composition includes at least one bioresorbable bead.

According to one aspect, a flowable birth tissue composition is provided that includes a mammalian placental tissue treated with a bioburden reduction step, a detergent treatment step, and a viral inactivation step. According to one embodiment, the mammalian placental tissue exhibits a pH of between about 6.8 and about 7.2. According to one embodiment, the mammalian placental tissue includes a dehydrated porcine placental membrane that includes collagen I, collagen IV, elastin, laminin, fibronectin and hyaluronic acid.

According to one aspect, a method of preparing a flowable birth tissue composition is provided. The method includes the steps of:
a) introducing from about 1 mL to about 40 mL of from about 1M to about 4M sodium chloride solution per gram of placental tissue to the placental tissue;
b) decanting the sodium chloride;
c) rinsing the sodium chloride from the placental tissue with water;
d) introducing from about 5 mL to about 25 mL of a detergent solution per gram of placental tissue to the placental tissue;
e) decanting the detergent solution;
f) rinsing the detergent solution from the placental tissue with water;
g) introducing from about 5 mL to about 15 mL of from about 0.1M to about 1.0M sodium hydroxide per gram of placental tissue to the placental tissue;
h) rinsing the sodium hydroxide from the placental tissue with water;
i) introducing from about 5 mL to about 50 mL of buffer solution per gram of placental tissue to the placental tissue;
j) decanting the buffer solution;
k) measuring the pH of the placental tissue;
l) repeating steps i), j) and k) until the pH of the placental tissue is between about 6.8 and about 7.2;
m) rinsing the buffer solution from the placental tissue with water;
n) milling the placental tissue to form a placental tissue powder; and
o) homogenizing a pharmaceutically-acceptable carrier with the placental tissue powder to form a flowable birth tissue composition. According to one embodiment, the method further includes the steps of:
p) packaging the flowable birth tissue composition; and
q) terminally sterilizing the packaged composition. According to one embodiment, the detergent solution includes at least one anionic detergent and at least one protease enzyme. According to one embodiment, the female mammal is a pig or human. According to one embodiment, the female pig is not genetically modified to halt or reduce expression of a functional alpha-1,3 galactosyltransferase gene. According to one embodiment, the flowable birth tissue composition is a liquid.

According to one aspect, a method of preparing a flowable birth tissue composition is provided that includes the steps of:
a) introducing from about 1 mL to about 40 mL of from about 1M to about 4M sodium chloride solution per gram of placental tissue to the placental tissue;
b) decanting the sodium chloride;
c) rinsing the sodium chloride from the placental tissue with water;
d) introducing from about 5 mL to about 25 mL of a detergent solution per gram of placental tissue to the placental tissue;
e) decanting the detergent solution;
f) rinsing the detergent solution from the placental tissue with water;
g) introducing from about 5 mL to about 15 mL of from about 0.1M to about 1.0M sodium hydroxide per gram of placental tissue to the placental tissue;
h) rinsing the sodium hydroxide from the placental tissue with water;
i) introducing from about 5 mL to about 50 mL of buffer solution per gram of placental tissue to the placental tissue;
j) decanting the buffer solution;
k) measuring the pH of the placental tissue;
l) repeating steps i), j) and k) until the pH of the placental tissue is between about 6.8 and about 7.2;
m) rinsing the buffer solution from the placental tissue with water;
n) milling the placental tissue to form a placental tissue powder;
o) mixing hyaluronic acid and a radioprotective solution to form a suspension gel; and
p) homogenizing the suspension gel with the placental tissue powder to form a flowable birth tissue composition. According to one embodiment, the method further includes the steps of:
q) packaging the flowable birth tissue composition; and
r) terminally sterilizing the packaged composition. According to one embodiment, the detergent solution includes at least one anionic detergent and at least one protease enzyme. According to one embodiment, the female mammal is a pig or human. According to one embodiment, the female pig is not genetically modified to halt or reduce expression of a functional alpha-1,3 galactosyltransferase gene. According to one embodiment, the flowable birth tissue composition is a gel.

A kit for bulking structural tissue is also provided. The kit includes a flowable birth tissue composition as provided herein. The kit may also include instructions for use. According to one embodiment, the kit may optionally include a syringe or cannula for delivery of the composition to a target site within a patient in need. According to one embodiment, the syringe or cannula is pre-loaded with a flowable birth tissue composition as provided herein.

According to one aspect, a method of bulking structural tissue is provided. According to one embodiment, the method includes the step of introducing a therapeutically effective amount of the flowable birth tissue composition as provided herein to a structural tissue within a patient in need.

According to one aspect, a method for vascular embolization is provided. The method includes the step of introducing the flowable birth tissue composition as provided herein to a blood vessel. According to one embodiment, the flowable birth tissue composition prevents blood flow to a target site.

According to another aspect, a porcine flowable birth tissue composition is provided that is produced by any of the aforementioned methods.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements.

As used in the specification, and in the appended claims, the singular forms "a", "an", "the", include plural referents unless the context clearly dictates otherwise. As used in the specification, and in the appended claims, the words "optional" or "optionally" mean that the subsequently described event or circumstance can or cannot occur.

The present disclosure provides a flowable birth tissue composition that is prepared from mammalian birth tissue. The present disclosure particularly provides a porcine birth tissue composition that is prepared from pig birth tissue.

As used to herein, the term "birth tissue composition" refers to a construct that is applied onto or around an injured area of a mammalian body.

As used herein, the terms "birth tissue" and "placental tissue" include, but are not limited to, elements of a mammalian placental organ such as, for example, mammalian placental membrane, mammalian amnion, mammalian chorion, mammalian intermediate layer, mammalian placental globe, mammalian umbilical cord, mammalian amniotic fluid, or a combination thereof.

As used herein, the term "placental membrane" refers to the full, intact placental membrane including the amnion and chorion layers that are obtained from a mammal such as, for example, a pig or human.

As used herein, the term "wound" refers to an injured area of the body.

As used herein, the term "flowable" refers to the ability of a composition as provided herein to flow or move. The birth tissue compositions as provided herein exhibit a liquid or gel viscosity appropriate for various regenerative medical applications.

As used herein, the terms "pig" and "porcine" may be used interchangeably.

The flowable birth tissue composition as provided herein may aid in the healing cascade or healing process of a mammalian wound. In a particular embodiment, the flowable birth tissue composition is fully resorbed by the mammal's body during the healing process. The present disclosure further relates to methods for aseptically processing birth tissue to produce a flowable birth tissue composition.

In one embodiment, the flowable birth tissue composition, such as a porcine birth tissue composition, may be used for a variety of regenerative medicine purposes. According to one embodiment, the regenerative medical use is for treatment of wounds. Other suitable uses include inflammation reduction (anti-inflammatory); pain reduction; anti-adhesion; skin wrinkle reduction, skin resurfacing, skin rejuvenation, and other cosmetic purposes; nerve repair; soft tissue repair; bone repair; joint pain treatment; dura preservation; ocular defect treatment and other similar regenerative uses. Exemplary wounds that may be treated with the birth tissue compositions as provided herein include partial and full thickness wounds; pressure ulcers; venous ulcers; diabetic ulcers; chronic vascular ulcers; tunneled/undermined wounds; surgical wounds (e.g., donor sites/grafts, post-Mohs surgery, post-laser surgery, podiatric, wound dehiscence); trauma wounds (e.g., abrasions, lacerations, second degree burns, skin tears); and draining wounds. The flowable birth tissue compositions may also be utilized on any wound arising on or around a soft tissue, nerve, organ, vascular tissue, muscle, spinal cord, bone, oral cavity, ocular surface, or a combination thereof.

The birth tissue composition as provided herein is formulated as a flowable construct. The flowable birth tissue composition may include any one or more of a variety of mammalian placental tissue such as, for example, mammalian placental membrane, mammalian amnion, mammalian chorion, mammalian intermediate layer, mammalian placental globe, mammalian umbilical cord, mammalian amniotic fluid or a combination thereof. The flowable birth tissue composition may include any variety of porcine birth tissue such as, for example, porcine placental membrane, porcine amnion, porcine chorion, porcine intermediate layer, porcine placental globe, porcine umbilical cord, porcine amniotic fluid or a combination thereof. The birth tissue composition as provided herein may be formulated as a gel, liquid or spray.

According to one embodiment, the flowable birth tissue compositions as provided herein may be treated to provide for the delivery of a variety of antibiotics, anti-inflammatory agents, growth factors and/or other specialized proteins or small molecules. A flowable birth tissue composition as described herein may be produced by processing mammalian birth tissue according to any or all of the steps provided herein as applied to birth tissue. According to a particular embodiment, a flowable birth tissue composition as described herein may be produced by processing pig or human birth tissue according to the steps provided herein.

According to one embodiment, a method of preparing a flowable birth tissue composition is provided. The method includes the step of collecting the placental tissue from a female mammal. According to one embodiment, the method includes the step of collecting the placental tissue from a female pig. According to one embodiment, the female pig is not genetically modified to halt or reduce expression of the functional alpha-1,3 galactosyltransferase gene. According to one embodiment, the placental tissue collected is the placental membrane with the umbilical cord attached. Potential placental tissue donors are screened and tested to exclude any donors that may present a health risk. According to one embodiment, placental tissue is recovered from a full-term delivery of one or more offspring such as an infant or piglet(s). According to one embodiment, the method further includes the step of placing the placental tissue in a transport container. According to one embodiment, the method further includes the step of placing the placental tissue in a transport container containing a transport solution. According to one embodiment, the method optionally includes the step of placing the amniotic fluid in a separate transport container.

According to one embodiment, the method further includes the step of rinsing the placental tissue with water. According to a particular embodiment, the water is sterile water. According to a particular embodiment, the water is type 1 water. According to one embodiment, the method further includes the step of removing a substantial portion of any residual moisture present on the placental tissue.

According to one embodiment, the method further includes the step of freezing the placental tissue. According to one embodiment, the placental tissue may be kept frozen until further processing. According to one embodiment, the method further includes the step of removing the frozen placental tissue from the freezer and thawing in a refrigerator for about three (3) to five (5) days. According to one embodiment, the method further includes the step of thawing the placental tissue at ambient temperature.

According to one embodiment, the method optionally includes the step of freezing the amniotic fluid or components thereof in a separate container from the placental tissue. According to one embodiment, the amniotic fluid may be kept frozen until further processing. According to another embodiment, the amniotic fluid may be sterile filtered and then subsequently frozen until further processing. According to another embodiment, the amniotic fluid may be centrifuged followed by removal of supernatant with the resulting amniotic fluid composition then stored for further processing. According to one embodiment, the method further includes the step of removing the frozen amniotic fluid or amniotic fluid composition from the freezer and thawing in a refrigerator for about three (3) to five (5) days. According to one embodiment, the method further includes the step of thawing the amniotic fluid or amniotic fluid composition at ambient temperature.

According to one embodiment, the method includes rinsing the placental tissue with water. According to a particular embodiment, the water is sterile water. According to one embodiment, the water is type 1 water. According to one embodiment, the method includes draining the placental tissue. According to one embodiment, the method includes the step of opening any tube-shaped placental tissue so the placental tissue will lie flat onto a cutting surface. According to one embodiment, the method includes separating the placental membrane from the umbilical cord.

According to one embodiment, the method includes the step of dividing the placental tissue into pieces. According to one embodiment, a rotary cutter or other suitable cutter is used to cut the pieces.

According to one embodiment, the method optionally includes the step of removing Wharton's jelly and excess fluids from the placental tissue to produce cleaned placental tissue. According to one embodiment, the method includes the step of weighing the cleaned placental tissue on a tared balance to determine the placental tissue wet weight.

According to one embodiment, the method includes the step of treating the placental tissue with a bioburden reduction solution. According to a particular embodiment, the bioburden reduction solution is sodium chloride. According to one embodiment, the method includes the step of adding from about 1 mL to about 40 mL of from about 1M to about 4M sodium chloride solution per gram of placental tissue to the cleaned placental tissue. According to one embodiment, the method includes the step of adding from about 5 mL to about 25 mL of 3M sodium chloride solution per gram of placental tissue to the cleaned placental tissue. According to one embodiment, the method includes the step of adding about 20 mL of 3M sodium chloride solution per gram of placental tissue to the cleaned placental tissue. According to one embodiment, the method includes the step of immersing the placental tissue in the sodium chloride solution from about thirty minutes to about two hours. According to a particular embodiment, the method includes the step of immersing the placental tissue in the sodium chloride solution for about one hour. According to one embodiment, the method includes the step of shaking the placental tissue in the sodium chloride solution from about thirty minutes to about two hours at about 50 RPM to about 100 RPM. According to a particular embodiment, the method includes the step of shaking the placental tissue in the sodium chloride solution for about one hour at about 50 RPM to about 100 RPM. According to one embodiment, the placental tissue is shaken on an orbital shaker table.

According to one embodiment, the method includes the step of decanting the sodium chloride. According to one embodiment, the method includes the step of rinsing the placental tissue with water. According to a particular embodiment, the water is sterile water. According to one embodiment, the water is type 1 water. According to a particular embodiment, the method includes the step of rinsing the placental tissue with from about 5 mL to about 25 mL of water per gram of placental tissue. According to a particular embodiment, the method includes the step of rinsing the placental tissue with about 20 mL of water per gram of placental tissue. According to one embodiment, the placental tissue is rinsed one time. According to one embodiment, the placental tissue is rinsed at least two times. According to one embodiment, the placental tissue is rinsed at least three times. According to one embodiment, the method includes the step of removing excess fluids from the placental tissue.

According to one embodiment, the method includes the step of placing the placental tissue in from about 5 mL to about 25 mL of a detergent solution. According to a particular embodiment, the method includes the step of placing the placental tissue in about 20 mL of a detergent solution. According to a particular embodiment, the method includes the step of placing the placental tissue in about 20 mL of a detergent solution per gram of placental tissue. According to one embodiment, the detergent is present at a concentration of about 0.25% to about 3% w/v. According to one embodiment, the detergent is present at a concentration of about 1% w/v. According to a particular embodiment, the detergent solution includes at least one anionic detergent and at least one protease enzyme. According to one embodiment, the detergent solution includes sodium linear alkylaryl sulfonate, phosphates, carbonates and at least one protease enzyme. According to one embodiment, the detergent solution is commercially available under the trade name Tergazyme™. According to one embodiment, the detergent solution is a 1% Tergazyme™ solution. According to one embodiment, the method includes the step of immersing the placental tissue in the detergent solution for from about one hour to about three hours. According to a particular embodiment, the method includes the step of immersing the placental tissue in the detergent solution for about two hours. According to one embodiment, the method includes the step of shaking the placental tissue in the detergent solution for from about one hour to about three hours at about 50 RPM to about 100 RPM. According to one embodiment, the method includes the step of shaking the placental tissue in the detergent solution for about two hours at about 50 RPM to about 100 RPM. According to one embodiment, the placental tissue is shaken on an orbital shaker table.

According to one embodiment, the method includes the step of decanting the detergent solution. According to one embodiment, the method includes the step of rinsing the placenta tissue with water. According to a particular embodiment, the water is sterile water. According to one embodiment, the water is type 1 water. According to one embodiment, the method includes the step of rinsing the placental tissue with from about 5 mL to about 25 mL of water per gram of placental tissue. According to one embodiment, the method includes the step of rinsing the placental tissue with about 20 mL of water per gram of placental tissue. According to one embodiment, the placental tissue is rinsed one time. According to one embodiment, the placental tissue is rinsed at least two times. According to one embodiment, the placental tissue is rinsed at least three times. According to one embodiment, the method includes the step of removing excess fluids from the placental tissue.

According to one embodiment, the method includes the step of treating the placental tissue with a viral inactivation solution. According to a particular embodiment, the viral inactivation solution is sodium hydroxide. According to one embodiment, the method includes the step of adding or introducing from about 5 mL to about 15 mL of about 0.1M to about 1.0M sodium hydroxide per gram of placental tissue. According to one embodiment, the method includes the step of adding or introducing from about 5 mL to about 15 mL of 0.25M sodium hydroxide per gram of placental tissue. According to one embodiment, the method includes the step of adding or introducing about 10 mL of 0.25M sodium hydroxide per gram of placental tissue. According to one embodiment, the method includes the step of immersing the placental tissue in the sodium hydroxide for about 15 minutes to about 45 minutes. According to one embodiment, the method includes the step of immersing the placental tissue in the sodium hydroxide for about 20 minutes. According to one embodiment, the method includes the step of shaking the placental tissue in the sodium hydroxide for about 15 minutes to about 45 minutes at about 50 RPM to about 100 RMP. According to one embodiment, the method includes the step of shaking the placental tissue in the sodium hydroxide for about 20 minutes at about 50 RPM to about 100 RPM. According to one embodiment, the placental tissue is shaken on an orbital shaker table. The sodium hydroxide may then be decanted. According to one embodiment, the steps of adding sodium hydroxide, shaking and decanting may be repeated as many times as necessary to inactivate any viruses present in the placental tissue to produce a placental tissue that is substantially void of viruses. According to one embodiment, the steps of adding sodium hydroxide, shaking and decanting may be repeated once. According to one embodiment, the steps of adding sodium hydroxide, shaking and decanting may be repeated twice.

According to one embodiment, the method includes the step of rinsing the placental tissue with water. According to a particular embodiment, the water is sterile water. According to one embodiment, the water is type 1 water. According to a particular embodiment, the step of rinsing the placental tissue with sterile water is carried out for up to about 10 minutes. According to one embodiment, the method includes the step of removing excess fluids from the placental tissue.

According to one embodiment, the method includes the step of adding or introducing from about 5 mL to about 50 mL of buffer solution per gram of placental tissue. According to a particular embodiment, the method includes the step of adding or introducing about 20 mL of buffer solution per gram of placental tissue. According to one embodiment, the method includes the step of immersing the placental tissue in the buffer solution. According to one embodiment, the method includes the step of shaking the placental tissue in the buffer solution for about 5 minutes to about 45 minutes at about 50 RPM to about 100 RPM. According to one embodiment, the method includes the step of shaking the placental tissue in the buffer solution for about 20 minutes at about 50 RPM to about 100 RPM. According to one embodiment, the placental tissue is shaken on an orbital shaker table. The buffer solution may then be decanted.

According to a particular embodiment, the buffer solution is phosphate-buffered saline. According to one embodiment, the method includes the step of measuring the pH of the placental tissue after buffer solution treatment. According to one embodiment, the steps of adding buffer solution, shaking and decanting may be repeated until the pH of the placental tissue is between about 6.8 and about 7.2.

According to one embodiment, the method includes the step of rinsing the placental tissue with water. According to a particular embodiment, the water is sterile water. According to one embodiment, the water is type 1 water. According to one embodiment, the placental tissue is rinsed one time. According to one embodiment, the rinsing step is carried out multiple times. According to a one embodiment, the rinsing step is carried out at least twice. According to a one embodiment, the rinsing step is carried out at least three times. According to one embodiment, the method further includes the step of removing a substantial portion of any residual moisture present in the placental tissue.

When preparing a flowable birth tissue composition the method optionally includes the step of dehydrating the placental tissue. According to one embodiment, the placental tissue may be dehydrated by any method known in the art, including, but not limited to, chemical dehydration (e.g., organic solvents), lyophilization, desiccation, oven dehydration and air drying. According to a particular embodiment, the method includes the step of adding or introducing an alcohol to the placental tissue to cover the entire surface of the placental tissue (i.e., submerge the placental tissue). According to one embodiment, the method includes the step of adding or introducing from about 1 mL to about 10 mL of alcohol per gram of placental tissue. According to one embodiment, the method includes the step of adding or introducing about 5 mL of alcohol per gram of placental tissue. According to one embodiment, the placental tissue is fully submerged in the alcohol for from about one hour to about 24 hours. According to one embodiment, the placental tissue is not agitated while in contact with the alcohol. The alcohol may be any alcohol which is and appropriate for contact with placental tissue. According to a particular embodiment, the alcohol is ethanol. According to another embodiment, the ethanol is from about 90%-100% ethanol.

According to a particular embodiment, the ethanol is 200 proof (i.e., absolute ethanol). According to one embodiment, the method includes the step of decanting or draining the alcohol from the placental tissue.

According to one embodiment, the optional dehydration method may be carried out by spreading the placental tissue onto a drying table. According to one embodiment, the placental tissue may be blotted with a micro fiber wipe or similar. The placental tissue may be spread in a manner so as to fully dehydrate the placental tissue while ensuring no wrinkles or bubbles are present.

According to one embodiment, the optional dehydration method may be carried out by lyophilizing the placental tissue. According to a particular embodiment, the method includes the steps of placing the placental tissue on a lyophilization tray and spreading the placental tissue out evenly. The tray containing the placental tissue may then be subject to a lyophilization drying cycle to produce a dehydrated placental tissue. The dehydrated placental tissue may be stored until further processing is required.

According to one embodiment, the method includes the step of milling or grinding the dehydrated placental tissue to form a placental tissue powder. According to one embodiment, the placental tissue may be micronized or otherwise rendered into fine particulates to form a placental tissue powder. Particles may be micron or submicron size. In one embodiment, the particle sizes may range from about 0.001 micrometer to about 1,000 micrometers. In a particular embodiment, the particle size is about 100 micrometers. In another embodiment, the particle sizes may range from about 1 nanometer to 100 nanometers. The particle size of the materials in the placental tissue powder can vary depending upon the clinical application of the flowable birth tissue composition.

According to one embodiment, the flowable birth tissue composition is prepared by mixing the placental tissue powder with at least one pharmaceutically-acceptable carrier. The pharmaceutically-acceptable carrier may be any pharmaceutically-acceptable carrier known in the art, including, but not limited to, e.g., water, saline, 0.9% sodium chloride injection, aqueous hyaluronic acid, dextrose solution, Hank's solution, Ringer's solution and other aqueous physiologically balanced salt solutions or a combination thereof. According to one embodiment, the pharmaceutically-acceptable carrier is amniotic fluid or a component thereof. According to one embodiment, the pharmaceutically-acceptable carrier is a radioprotective solution, which may be any suitable solution that protects the placental tissue powder from the effects of radiation. The radioprotective solution may include any one or more of a variety of radioprotective solutions known in the art, including, but not limited to, e.g., glycerol (5%-70% by volume); propylene glycol (1%-30% by volume); trehalose/mycose (1%-30% by weight); dextrose (10%-70% by weight); glucose (10%-70% by weight); sucrose (10%-70% by weight); dimethyl sulfoxide (0.1%-10% by volume); albumin (1%-50% by volume); hyaluronic acid (1%-70% by volume); sodium hyaluronate (0.1 kDa-2.0 MDa); and sulfhydrl compounds and derivatives thereof.

It will be appreciated that the concentration of placental tissue powder in relation to the concentration of pharmaceutically-acceptable carrier will vary according to the particular composition formulation, the mode of application, and the particular situs and subject being treated. According to a particular embodiment, the method includes the step of introducing from about 0.001 g to about 2.0 g of the placental tissue powder to from about 0.1 mL to about 1 mL of at least one pharmaceutically-acceptable carrier. According to one embodiment, the placental tissue powder is introduced at a rate such that the resulting composition includes the placental tissue powder at a concentration of from about 0.01 g/mL to about 2.0 g/mL. According to a particular embodiment, the placental tissue powder is introduced at a rate such that the resulting composition includes placental tissue powder at a concentration of about 0.50 g/mL. According to a particular embodiment, the flowable birth tissue composition is formulated by homogenizing or otherwise mixing the placental tissue powder with a pharmaceutically-acceptable carrier based on the equation of one part of placental tissue wet weight to two parts pharmaceutically-acceptable carrier.

According to an alternate embodiment, the method includes the step of adding from about 0.001 g to about 0.1 g of hyaluronic acid to from about 0.1 mL to about 1.0 mL of a radioprotective solution to form a suspension gel. The hyaluronic acid is any suitable hyaluronic acid form, including, but not limited to, aqueous hyaluronic acid, hyaluronic acid powder, hyaluronic acid hydrogel, or sodium hyaluronate. The radioprotective solution is any suitable solution that protects a tissue from the effects of radiation. The radioprotective solution may include any one or more of a variety of radioprotective solutions known in the art, including, but not limited to, e.g., glycerol (5%-70% by volume); propylene glycol (1%-30% by volume); trehalose/mycose (1%-30% by weight); dextrose (10%-70% by weight); glucose (10%-70% by weight); sucrose (10%-70% by weight); dimethyl sulfoxide (0.1%-10% by volume); albumin (1%-50% by volume); hyaluronic acid (1%-70% by volume); sodium hyaluronate (0.1 kDa-2.0 MDa); and sulfhydrl compounds and derivatives thereof.

According to one embodiment, the method includes the step of adding from about 0.001 g to about 2.0 g of the placental tissue powder as provided herein to from about 0.1 mL to about 1.0 mL of the suspension gel.

According to one embodiment, the method includes the step of homogenizing or otherwise mixing the placental tissue powder with the suspension gel to form a flowable birth tissue composition. According to a particular embodiment, the flowable birth tissue composition is formulated by homogenizing or otherwise mixing the placental tissue powder with a suspension gel based on the equation of one part of placental tissue wet weight to two parts suspension gel.

The flowable birth tissue compositions as provided herein may be mixed with, absorbed within, taken up by, or applied to at least one bioresorbable bead as provided herein. The bioresorbable bead may include one or more compounds that break down or may be absorbed or otherwise disposed of by the human body, including, bioresorbable beads composed of polymers and monomers, e.g., ethane, paraffin, polyethylene, glycogen, propylene, vinyl chloride, tetrafluoroethylene, and monosaccharides. According to a particular embodiment, the bioresorbable bead includes one or more of chitosan and cellulose compounds that eventually break down into molecules that the human body can process. The size of the at least one bead with the birth tissue composition as provided herein is small enough such that the resulting flowable birth tissue composition may enter and flow through a needle or cannula such as, for example, a 33-gauge needle or cannula.

According to one embodiment, the at least one bioresorbable bead as provided herein is a microbead. According to one embodiment, the at least one bioresorbable bead is a nanobead. According to one embodiment, the at least one bioresorbable bead is from about 0.01 micrometer to about 500 micrometers in diameter. According to one embodiment, the at least one bioresorbable bead is from about 0.1 micrometer to about 250 micrometers in diameter. According to one embodiment, the at least one bead is a bioresorbable poly(2-hydroxyethyl methacrylate) nanobead. According to one embodiment, the at least one bead is a recombinant bioresorbable microbead, e.g., a microbead composed of protein disulfide-isomerase (P4HB), poly-L-lactic add (PLLA), or poly(lactic-co-glycolic acid) (PLGA).

According to one embodiment, the flowable birth tissue composition as provided herein may be placed in a proper package. A suitable package includes a vial or a pre-loaded cannula or syringe. According to one embodiment, the chosen package may then be placed into and sealed within an outer package.

According to one embodiment, the method includes the step of terminally sterilizing the packaged flowable birth tissue composition. According to one embodiment, the method of terminal sterilization may be e-beam irradiation, gamma irradiation, peracetic acid treatment, vaporized peracetic acid (VPA) treatment, any combination thereof, or any other terminal sterilization method known in the art.

According to one embodiment, the dehydrated porcine placental membranes utilized in the formation of the flowable birth tissue compositions as provided herein include one or more of collagen I, collagen IV, elastin, laminin, fibronectin and hyaluronic acid. According to one embodiment, each of the one or more of collagen I, collagen IV, elastin, laminin, fibronectin and hyaluronic acid is present in the dehydrated porcine placental membrane in an amount that is different from a porcine placental membrane that is not processed according to one or more of the processing steps provided herein. According to one embodiment, collagen I is present in an amount of from about 0.001% w/w to about 99.9% w/w based on the total weight of the placental membrane. According to one embodiment, collagen IV is present in an amount of from about 0.001% w/w to about 99.9% w/w based on the total weight of the placental membrane. According to one embodiment, elastin is present in an amount of from about 0.001% w/w to about 99.9% w/w based on the total weight of the placental membrane. According to one embodiment, laminin is present in an amount of from about 0.001% w/w to about 99.9% w/w based on the total weight of the placental membrane. According to one embodiment, fibronectin is present in an amount of from about 0.001% w/w to about 99.9% w/w based on the total weight of the placental membrane. According to one embodiment, hyaluronic acid is present in an amount of from about 0.001% w/w to about 99.9% w/w based on the total weight of the placental membrane.

A method of treating a wound is also provided. According to one embodiment, the method includes the step of providing a flowable birth tissue composition as provided herein. The flowable birth tissue composition is then placed on or around a wound. According to one embodiment, the flowable birth tissue composition is injected directly in the wound or around the wound. The wound may be a burn, cut, abrasion, tissue void, or ulcer. According to one embodiment, the wound may be a surgical site anywhere on a mammalian body. The flowable birth tissue composition can also be used to cover an implant or other device that may be placed on or within a mammalian body.

The flowable birth tissue composition as provided herein may be utilized for various medical purposes where bulking or weighting of a target tissue is needed. The flowable birth tissue composition provides weight or bulking but does not migrate within a patient's body.

A method of bulking structural tissue is also provided. Such bulking is particularly useful in cosmetic surgery or other cosmetic applications. The method includes the step of introducing a therapeutically effective amount of a flowable birth tissue composition as provided herein to a structural tissue within a patient in need. According to one embodiment, the flowable birth tissue composition for bulking structural tissue may include one or more bioresorbable beads as provided herein. The bulking of tissue is particularly useful in various cosmetic applications where increasing the weight of a tissue is required. Suitable cosmetic applications include treatment of rhytids (e.g., crow's feet, marionette marks, neck bands, frown lines), elastosis (e.g., face and neck), and lip augmentation.

A method of vascular embolization is also provided. The method includes the step of introducing a therapeutically effective amount of the flowable birth tissue composition as provided herein to a blood vessel within a patient in need. According to one embodiment, the flowable birth tissue composition for vascular embolization may include one or more bioresorbable beads as provided herein. Upon introduction, the flowable birth tissue composition prevents blood flow to a target site.

The flowable birth tissue composition as provided herein may also be utilized for various urogynecological applications such as for repairs to the bladder, pelvic floor or urethra. According to a particular embodiment, the flowable birth tissue composition as provided herein may be utilized for penile enhancement and/or erectile dysfunction. According to one embodiment, the flowable birth tissue composition for penile enhancement and/or erectile dysfunction may include one or more bioresorbable beads as provided herein. According to such an embodiment, the method includes the step of introducing a therapeutically effective amount of the flowable birth tissue composition as provided herein to the penis of a patient in need of treatment.

According to a one embodiment, a therapeutically effective amount of the flowable birth tissue composition as provided herein may be utilized for vaginoplasty within a patient in need. According to one embodiment, the flowable birth tissue composition for vaginoplasty may include one or more bioresorbable beads as provided herein. According to such an embodiment, the method includes the step of introducing a therapeutically effective amount of the flowable birth tissue composition as provided herein to the vagina of a patient in need to reconstruct the vagina.

According to a one embodiment, the flowable birth tissue compositions as provided herein may be utilized to treat stress urinary incontinence by aiding in keeping the ureter straight. According to one embodiment, the flowable birth tissue composition for stress urinary incontinence may include one or more bioresorbable beads as provided herein. According to such an embodiment, the method includes the step of introducing a therapeutically effective amount of the flowable birth tissue composition as provided herein to the ureter or an area surrounding the ureter within a patient in need.

According to one embodiment, a therapeutically effective amount of the flowable birth tissue composition as provided herein may be utilized to repair and reconstruct prostate glands within a patient in need. The flowable birth tissue composition creates fibrous ingrowth and bulking after a prostatectomy. According to one embodiment, the flowable birth tissue composition for repairing and reconstructing prostate glands may include one or more bioresorbable beads as provided herein. According to such an embodiment, the method includes the step of introducing a therapeutically effective amount of the flowable birth tissue composition as provided herein to or around a prostate gland within a patient in need.

A kit for bulking structural tissue is also provided. The kit includes a flowable birth tissue composition as provided herein. The kit may also include instructions for use. According to one embodiment, the flowable birth tissue composition included in the kit may include one or more bioresorbable beads as provided herein. According to one embodiment, the kit may optionally include a syringe or cannula for delivery of a birth tissue composition as provided herein to a target site within a patient in need. According to one embodiment, the syringe or cannula is pre-loaded with a therapeutically effective amount of a flowable birth tissue composition as provided herein.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Example 1

Porcine placental membrane processed according to the methods as provided herein. Particularly, porcine placental membrane was treated with a bioburden solution, treated with a detergent solution, treated with a viral inactivation solution and dehydrated according the methods as provided herein. The resulting dehydrated porcine placental membrane was analyzed to assess the presence of the following extracellular matrix components: collagen I, collagen IV, elastin, laminin, fibronectin, and hyaluronic acid (HA). An immunostaining procedure was carried out utilizing a primary antibody to detect the specific protein in the sample and then a secondary antibody was labeled with a fluorophore to detect any bound primary antibody. Utilizing this methodology enabled improved detection of the primary antibodies since two or more secondary antibodies can detect a single primary antibody and thereby increase the fluorescent signal for imaging.

The following primary antibodies were used:
Rabbit Anti-Collagen I antibody (Cat #ab34710 Abcam, Cambridge, Mass., USA)
Rabbit Anti-Collagen IV antibody (Cat #ab6586 Abcam, Cambridge, Mass., USA)
Rabbit Anti-Elastin antibody (Cat #ab21610 Abcam, Cambridge, Mass., USA)
Rabbit Anti-Laminin antibody (Cat #ab11575 Abcam, Cambridge, Mass., USA)
Rabbit Anti-Fibronectin antibody (Cat #ab2413 Abcam, Cambridge, Mass., USA)
Mouse Anti-Hyaluronic Acid antibody (Cat #CAU29210 Biomatik, Wlimgton, Del., USA)

The following secondary antibodies were used:
Anti-Rabbit 488 secondary antibody (provided by the Integrated Microscopy Center, The University of Memphis, Memphis, Tenn., USA).
Anti-Mouse 594 secondary antibody (provided by the Integrated Microscopy Center, The University of Memphis, Memphis, Tenn., USA).

One centimeter diameter samples were cut at random from ten sterile porcine placental membrane samples (approximately 2.5 cm diameter by <0.5 mm thick). Triplicate samples were evaluated for each matrix component. Samples were attached to cover slips (approximately 2 cm diameter) using phosphate buffered saline (PBS). The samples were allowed to dry at ambient conditions overnight. Samples were then were soaked in 1% NP-40 (a detergent used to increase permeability of biological specimen for staining procedures) for 5 minutes and then rinsed three times with approximately 1 ml of PBS. The primary antibodies for collagen I, collagen IV, elastin, laminin, fibronectin, and hyaluronic acid (HA) were diluted 1:20 in PBS. The samples were covered with 50 µl of the primary antibody dilutions and incubated overnight at 4° C. The next day, the samples were rinsed three times with approximately 1 ml PBS to remove unbound primary antibodies. The secondary antibodies were diluted 1:50 in PBS and the samples were covered with 50 µl of the secondary antibodies. The anti-rabbit 488 secondary antibody was used for the collagen I, collagen IV, elastin, fibronectin, and laminin samples. The anti-mouse 594 secondary antibody was used for the hyaluronic acid (HA) sample. After 1 hour of incubation at 4° C., the samples were again rinsed three times with 1 ml PBS to remove unbound secondary antibodies. The coverslips were mounted to slides (7.5 cm long×2.5 cm wide) using Slowfade Diamond Antifade Mountant (Fisher Scientific). Slides were examined using a confocal laser scanning microscope (Ti-E A1rSi System, Nikon Instruments, Inc. Melville, N.Y., USA) at 20× magnification. Secondary only controls (sections stained only with the secondary antibodies) were used to adjust brightness and intensity to account for any background fluorescence due to non-specific antibody absorption on to samples. Brightness and intensity settings were kept uniform so that images from all groups could be compared. Samples were imaged using optical sectioning. For the optical sectioning, between 35-55 slices or planes of focus were collected starting at the surface and moving into the sample at approximately 0.51 µm intervals. The collected images were stacked to create a composite image. There were n=3 images collected for each extracellular matrix component evaluated.

The sterilized porcine placental membranes showed positive staining for each of collagen I, collagen IV, elastin, laminin, fibronectin, and hyaluronic acid (HA). Collagen I and collagen IV showed the highest intensity of staining, although all antibodies did show positive staining. Based on the immunostaining, the porcine placental membranes processed according to the methods as provided herein contained collagen I, collagen IV, elastin, laminin, fibronectin, and hyaluronic acid (HA).

Example 2

An eighteen-year-old thoroughbred gelding horse suffered a plantar injury during a polo match. The horse was diagnosed with core lesion plantar/tuber aspect of superficial digital flexor (SDF), 20-28 cm from point of hock and presented with heat, swelling and lameness as a result of the injury. Approximately six months after injury, a general examination to determine overall health of the patient was conducted. Excluding the noted injury, the general health and condition of the horse was good. The horse appeared bright and alert with temperature, respiratory and heart rate within a normal range. An ultrasound was used to confirm diagnosis and location of injury. An injection site was prepared by sterilizing using surgical scrub. The horse was given a sedative for the safety and accuracy of the procedure. A flowable birth tissue composition in the form of a liquid was directly injected into the tendon and multiple locations along the affected area. After treatment, the horse was confined to a stall for three days. After three days the horse was let out into a small run. Size of turnout was increased over next 30 days. On the fourth day post injection, ice and hydro therapy was administered once a day for 15 minutes. While swelling and heat in the injured area increased for the first 48 hours after treatment, the injured area showed significant improvement (from both general examination and ultrasound imaging) approximately five weeks after treatment. The horse was expected to return to polo competition.

We claim:

1. A flowable porcine birth tissue composition comprising detergent-treated, milled porcine placental tissue; and
at least one carrier,
wherein the placental tissue is mixed with the at least one carrier to form the flowable porcine birth tissue composition, and
wherein the detergent includes at least one anionic detergent and at least one protease enzyme.

2. The flowable porcine birth tissue composition of claim 1, wherein the porcine placental tissue includes at least one placental membrane, at least one amnion membrane, at least one chorion membrane, at least one intermediate layer, at least one placental globe, at least one umbilical cord, at least one amniotic fluid, or any combination thereof.

3. The flowable birth tissue composition of claim 1, further comprising at least one bioresorbable bead.

4. The flowable porcine birth tissue composition of claim 1, wherein the porcine placental tissue exhibits a pH of between about 6.8 and about 7.2.

5. The flowable porcine birth tissue composition of claim 1, wherein the porcine placental tissue includes a dehydrated porcine placental membrane comprising collagen I, collagen IV, elastin, laminin, fibronectin and hyaluronic acid.

6. The flowable porcine birth tissue composition of claim 1, wherein the porcine placental tissue is derived from a female pig that is not genetically modified to halt or reduce expression of a functional alpha-1,3 galactosyltransferase gene.

7. The flowable porcine birth tissue composition of claim 1, wherein the flowable porcine birth tissue composition is formulated as a gel.

8. The flowable porcine birth tissue composition of claim 1, wherein the at least one carrier comprises water, saline, 0.9% sodium chloride injection, aqueous hyaluronic acid, dextrose solution, amniotic fluid, Hank's solution, Ringer's solution, or any combination thereof.

9. The flowable porcine birth tissue composition of claim 1, wherein the milled porcine placental tissue is present in an amount of from about 0.01 g/mL to about 2.0 g/mL of flowable porcine birth tissue composition.

10. The flowable porcine birth tissue composition of claim 5, wherein the collagen I, collagen IV, elastin, laminin, fibronectin and hyaluronic acid are present in the dehydrated porcine placental membrane in an amount that is different from native porcine placental membrane.

* * * * *